United States Patent
Suzuki et al.

(10) Patent No.: US 12,240,919 B2
(45) Date of Patent: Mar. 4, 2025

(54) METHOD FOR SUPPORTING THIOL GROUP-INCLUDING COMPOUND

(71) Applicant: KANEKA CORPORATION, Osaka (JP)

(72) Inventors: Takuma Suzuki, Settsu (JP); Dai Murata, Takasago (JP); Masakatsu Nishihachijyo, Takasago (JP); Hisako Yaura, Takasago (JP)

(73) Assignee: KANEKA CORPORATION, Osaka (JP)

( * ) Notice: Subject to any disclaimer, the term of this patent is extended or adjusted under 35 U.S.C. 154(b) by 779 days.

(21) Appl. No.: 17/434,039

(22) PCT Filed: Feb. 27, 2020

(86) PCT No.: PCT/JP2020/008017
§ 371 (c)(1),
(2) Date: Aug. 26, 2021

(87) PCT Pub. No.: WO2020/195514
PCT Pub. Date: Oct. 1, 2020

(65) Prior Publication Data
US 2022/0135705 A1 May 5, 2022

(30) Foreign Application Priority Data
Mar. 26, 2019 (JP) ................. 2019-057650

(51) Int. Cl.
*C07K 17/14* (2006.01)
*C07K 1/22* (2006.01)

(52) U.S. Cl.
CPC ........... *C07K 17/14* (2013.01); *C07K 1/22* (2013.01)

(58) Field of Classification Search
CPC ............ C07K 2319/23; C07K 2319/00; C07K 17/12; C07K 2319/31; C07K 1/1072; B82Y 15/00

USPC ........................................................ 435/510
See application file for complete search history.

(56) References Cited

U.S. PATENT DOCUMENTS

| 6,252,054 B1 | 6/2001 | Ogino et al. |
| 2016/0108127 A1 | 4/2016 | Brower et al. |
| 2020/0299402 A1 | 9/2020 | Brower et al. |

FOREIGN PATENT DOCUMENTS

| JP | 2000-154200 A | 6/2000 |
| JP | 2012-1462 A | 1/2012 |
| JP | 2014-210733 A | 11/2014 |
| JP | 2017-518293 A | 7/2017 |

OTHER PUBLICATIONS

Hober et al., "Protein A chromatography for antibody purification", Journal of Chromatography B, 2007, vol. 848, pp. 40-47.
International Search Report (PCT/ISA/210) issued in PCT/JP2020/008017 mailed on May 19, 2020.
Shukla et al., "Recent advances in large-scale production of monoclonal antibodies and related proteins", Trends in Biotechnology, 2010, vol. 28, No. 5, pp. 253-261.
Written Opinion (PCT/ISA/237) issued in PCT/JP2020/008017 mailed on May 19, 2020.

*Primary Examiner* — Tekchand Saidha
*Assistant Examiner* — Mohammad Y Meah
(74) *Attorney, Agent, or Firm* — Birch, Stewart, Kolasch & Birch, LLP

(57) ABSTRACT

The objective of the present invention is to provide a method for efficiently supporting a thiol group-including compound on an insoluble base material. The method for supporting a thiol group-including compound on an insoluble base material according to the present invention is characterized in comprising Step A: treating the thiol group-including compound with a thiol group-including organic reducing agent and an inorganic reducing agent, and Step B: contacting a reaction liquid of said Step A with the insoluble base material.

19 Claims, No Drawings

METHOD FOR SUPPORTING THIOL GROUP-INCLUDING COMPOUND

TECHNICAL FIELD

The present invention relates to a method for efficiently supporting a thiol group-including compound on an insoluble base material.

TECHNICAL FIELD

A thiol group reacts to a reactive functional group to form a covalent bond, since a thiol group is nucleophilic due to an unshared electron pair. Such a reaction is used for binding a thiol group-including compound to a base material. For example, many peptides contain a cysteine residue, and a cysteine residue has a thiol group in the side chain. Thus, a peptide is supported on an insoluble base material having a reactive functional group such as an epoxy group and an aldehyde group on the surface, and the base material is used as a carrier utilizing a function of the peptide (Patent document 1).

One of important functions of a protein is exemplified by a function to specifically bind to a specific molecule. The function plays an important role for an immune reaction and a signal transduction in a living body. A technology to utilize such a function for separating and purifying a useful substance has been actively developed. One example that is actually industrially used includes a Protein A affinity separation matrix. Protein A specifically binds to an Fc region of an antibody and is supported on the matrix. The matrix is used for purifying an antibody drug by capturing the antibody drug from an animal cell culture material at a time with high purity (Non-patent documents 1 and 2).

It is known that an unintended disulfide bond between thiol groups is formed in the case where a peptide is supported on a base material through a thiol group. When a disulfide bond is formed between peptides or in one peptide molecule, the peptide cannot be naturally reacted with a base material; as a result, a support yield becomes decreased. It is accordingly described in Patent document 2 that when a peptide is bound to a base material, an atmosphere is adjusted to be reductive and a thiol compound is added as a reducing agent so that a disulfide bond is not formed. Patent document 3 discloses that an SH group-including compound is reacted with a solvent-insoluble base material in the presence of an antioxidant agent. Patent document 4 discloses a method for controlling the number of a disulfide bond between polypeptides of a protein multimer by a redox agent.

PRIOR ART DOCUMENT

Patent Document

Patent document 1: JP 2012-1462 A
Patent document 2: JP 2014-210733 A
Patent document 3: JP 2000-154200 A
Patent document 4: JP 2017-518293 T

Non-Patent Document

Non-patent document 1: Hober S. et al., J. Chromatogr. B, 2007, vol. 848, pp. 40-47
Non-patent document 2: Shukla A. A. et al., Trends Biotechnol., 2010, vol. 28, pp. 253-261

DISCLOSURE OF THE INVENTION

Problems to be Solved by the Invention

The problem of a disulfide bond formation in the case where a thiol group-including compound is supported on an insoluble base material having a reactive functional group on the surface is recognized, and it is known to conduct the reaction under a reductive atmosphere and in the presence of a reducing agent as described above. On the one hand, since a demand of a carrier prepared by supporting a useful peptide on an insoluble base material is increased due to the development of an antibody drug or the like, an efficient method for supporting a thiol group-including compound on an insoluble base material is required to be further improved.

Accordingly, an objective of the present invention is to provide a method for efficiently supporting a thiol group-including compound on an insoluble base material.

Means for Solving the Problems

The inventors of the present invention repeated intensive studies in order to solve the above-described problems. As a result, the inventors completed the present invention by finding that a thiol group-including compound can be efficiently supported on an insoluble base material by using specific reducing agents in combination.

The present invention is hereinafter described.

[1] A method for supporting a thiol group-including compound on an insoluble base material, the method comprising:
  Step A: treating the thiol group-including compound with a thiol group-including organic reducing agent and an inorganic reducing agent, and
  Step B: contacting a reaction liquid of said Step A with the insoluble base material.

[2] The method according to the above [1], wherein the number of the thiol group in the thiol group-including organic reducing agent to 1 mole of the thiol group in the thiol group-including compound is 1 time or more by mole.

[3] The method according to the above [1] or [2], wherein 1 time or more by mole of the inorganic reducing agent is used to the 1 mole of the thiol group in the thiol group-including compound.

[4] The method according to any one of the above [1] to [3], wherein the thiol group-including compound is a thiol group-including peptide.

[5] The method according to any one of the above [1] to [4], wherein the thiol group-including organic reducing agent is dithiothreitol.

[6] The method according to any one of the above [1] to [5], wherein the inorganic reducing agent is one or more of inorganic reducing agents selected from the group consisting of a sulfite salt, a bisulfite salt, a pyrosulfite salt, a thiosulfate salt and a dithionite salt.

[7] The method according to any one of the above [1] to [6], wherein said Step A and said Step B are implemented under an air atmosphere.

Effect of the Invention

A misfolding and a dimerization of a thiol group-including compound due to a formation of a disulfide bond can be effectively suppressed by the present invention method. In addition, a thiol group-including compound can be efficiently supported on an insoluble base material, since a thiol group-including compound can be supported on an insoluble base material while a disulfide bond of the thiol group-including compound is suppressed in one reaction system. The present invention is, therefore, industrially useful, since an affinity separation matrix or the like usable for purifying an antibody and an antibody fragment can be efficiently produced by the present invention.

MODE FOR CARRYING OUT THE INVENTION

Each step of the present invention is hereinafter described, and the present invention is not restricted to the following description.

Step A: Step for Reduction

A disulfide bond formed between thiol group-including compound molecules or in one thiol group-including compound molecule is reduced to obtain the thiol group-including compound or a formation of a disulfide bond between thiol group-including compound molecules or in one thiol group-including compound molecule is suppressed by treating the thiol group-including compound with a thiol group-including organic reducing agent and an inorganic reducing agent in Step A.

The thiol group-including compound is not particularly restricted as long as the compound has one or more thiol groups (—SH). The thiol group may become —S⁻ depending on pH or the like in the reaction liquid or may further form a salt with a sodium ion, and the groups are included in the range of the thiol group in this disclosure.

An example of the thiol group-including compound includes a peptide comprising a thiol group; a low molecular organic compound comprising a thiol group, such as cysteine, ethanethiol, aminoethanethiol, benzylthiol and thiophenol; and a high molecular organic compound comprising a thiol group, such as polyethylene glycol and polyvinyl alcohol of which one or more hydroxy groups are transformed into thiol groups. A peptide means any molecules having a polypeptide structure, and any of an oligo peptide, a protein, a fragmented protein and two or more peptides linked with a peptide bond are included in the peptide. An example of the fragmented protein includes a domain. The term "domain" means a unit of higher-order structure of a protein. For example, a domain is composed of from dozens to hundreds of amino acid residues, and means a protein unit that can sufficiently serve some kind of a physicochemical function or a biochemical function.

A compound that specifically binds to the thiol group-including compound can be efficiently purified and detected by using a carrier on which the thiol group-including compound that has a specific affinity for the specific compound. For example, a peptide that specifically binds to an antibody or a part thereof is supported as the thiol group-including compound on an insoluble base material, and the obtained carrier can be used for purifying the antibody and part thereof. An example of such a thiol group-including compound includes Protein A, Protein G, Protein L and variants thereof. Protein A specifically binds to an Fc region. Protein G specifically binds to an Fc region and weakly binds to a Fab region. Protein L specifically binds to a K light chain.

The thiol group-including organic reducing agent means an organic compound that has one or more thiol groups and that shows a reduction action. An example of the thiol group-including organic reducing agent includes dithiothreitol, dithioerythritol, cysteine, N-acetyl-L-cysteine, 2-mercaptoethanol, reduced glutathione, 2-mercaptoethylamine and 1-thioglycerol. The thiol group-including organic reducing agent is particularly preferably dithiothreitol. Dithio-threitol has a stable 6-membered cyclic structure as described below and prevents a disulfide bond from being formed again after dithiothreitol reduces a disulfide bond formed by the thiol group-including compound. Dithioerythritol, which is an epimer of dithiothreitol, forms a similar 6-membered cyclic structure after exerting a reduction action but a reduction ability of dithioerythritol fall well short of that of dithiothreitol.

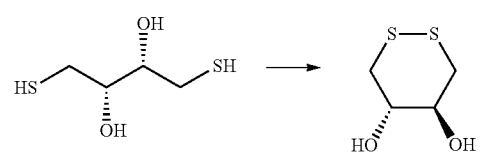 [SMILES: O[C@H](CS)[C@H](O)CS ; O[C@@H]1CSSC[C@H]1O]

The inorganic reducing agent is not particularly restricted as long as the inorganic reducing agent is an inorganic compound having a reduction action. An example of the inorganic reducing agent includes one or more inorganic reducing agents selected from the group consisting of a salt of sulfite ($SO_3^{2-}$), a salt of bisulfite ($HSO_3^-$), a salt of pyrosulfite ($S_2O_5^{2-}$), a salt of thiosulfate ($S_2O_3^{2-}$) and a salt of dithionite ($S_2O_4^{2-}$). A counter cation of the inorganic reducing agent is exemplified by an alkali metal ion such as sodium ion and potassium ion, and is preferably sodium ion from the viewpoint of cost.

A reaction condition of Step A may be appropriately adjusted in the range that a disulfide bond between the thiol group-including compound molecules or in one thiol group-including compound molecule can be reduced and/or the thiol group of the thiol group-including compound can be maintained.

For example, water may be mainly used as a solvent. When a solubility of the thiol group-including compound in water is not sufficient, a water-miscible organic solvent may be used in combination. A water-miscible organic solvent means an organic solvent that is mixed with water without restriction. An example of the water-miscible organic solvent includes an alcohol solvent such as methanol, ethanol and isopropanol; a ketone solvent such as acetone; an amide solvent such as dimethylformamide and dimethylacetamide; and a sulfoxide solvent such as dimethylsulfoxide. A pH of the reaction liquid is preferably adjusted to 6 or more and 11 or less, and the pH is more preferably 7 or more. A buffer solution having a pH in the above range may be used as the solvent. When the water-miscible organic solvent is used in combination, a ratio of the water-miscible organic solvent to a total of water and the water-miscible organic solvent may be appropriately adjusted and may be adjusted to, for example, 0.1 mass % or more and 80 mass % or less. The ratio is preferably 0.5 mass % or more, more preferably 1 mass % or more, and preferably 50 mass % or less, more preferably 20 mass % or less or 10 mass % or less, even more preferably 5 mass % or less or 2 mass % or less.

A concentration of the thiol group-including compound in the reaction liquid of Step A may be appropriately adjusted in the range that the thiol group of the thiol group-including compound is maintained. The concentration may be adjusted to, for example, 0.1 mg/mL or more and 100 mg/mL or less and is preferably 0.5 mg/mL or more and 70 mg/mL or less.

The thiol group-including organic reducing agent is excellent in a reduction action to a disulfide bond and a function to maintain a thiol group. On the one hand, when the thiol group-including organic reducing agent remains at the time of supporting the thiol group-including compound on the insoluble base material, the thiol group-including organic reducing agent may be supported on the insoluble base material; as a result, a yield of the target carrier may be decreased in some cases. Thus, it is considered that the oxidized thiol group-including organic reducing agent and the excessive thiol group-including organic reducing agent are removed after the thiol group-including compound is treated with the thiol group-including organic reducing agent, but such a removal involves trouble and cost and additionally the thiol group-including compound may form disulfide bond after the removal in some cases. Thus, the inorganic reducing agent is used in addition to the thiol group-including organic reducing agent in combination in the present invention.

A use amount of the thiol group-including organic reducing agent is preferably adjusted so that the number of the thiol group in the thiol group-including organic reducing agent to 1 mole of the thiol group in the thiol group-including compound becomes 1 time or more by mole and 8 times or less by mole. When the number is 1 time or more by mole, the disulfide bond may be reduced more surely and the formation of a disulfide bond by the thiol group-including compound may be suppressed more surely. When the number is 8 times or less by mole, the yield of the target carrier on which the thiol group-including compound is supported may be further increased. The number is more preferably 5 times or less by mole.

A use amount of the inorganic reducing agent to 1 mole of the thiol group in the thiol group-including compound is preferably 1 time or more by mole and 50 times or less by mole. When the ratio is 1 time or more by mole, a disulfide bond may be reduced more surely and the formation of a disulfide bond by the thiol group-including compound may be suppressed more surely. When the ratio is excessively large, the effect may be saturated; therefore, the ratio is preferably 50 times or less by mole. The ratio is more preferably 2 times or more by mole and 10 times or less by mole.

A reaction temperature of Step A may be adjusted to, for example, 1° C. or higher and 40° C. or lower. A reaction time may be adjusted to, for example, 10 minutes or more and 120 hours or less. Step A is not needed to be implemented under a reductive atmosphere and may be implemented under an oxidative atmosphere such as an air atmosphere, since a formation of a disulfide bond by the thiol group-including compound is suppressed due to the existence of the thiol group-including organic reducing agent and the inorganic reducing agent.

Step B: Supporting Step

The reaction liquid of Step A is contacted with an insoluble base material in Step B. Specifically, an insoluble base material or a dispersion liquid thereof may be added to the reaction liquid of Step A, the reaction liquid of Step A may be mixed with an insoluble base material or a dispersion liquid thereof, or the reaction liquid of Step A may be added to an insoluble base material or a dispersion liquid thereof. The reducing agent is not needed to be removed from the reaction liquid of Step A in any cases, and Step A and Step B may be implemented in the same system, in other words, in a one-pot manner.

The insoluble base material is not particularly restricted as long as the insoluble base material is insoluble in water and an organic solvent, and the thiol group-including compound can be supported on the insoluble base material. The insoluble base material may be an inorganic base material, an organic base material or a composite base material such as an organic-organic base material and an organic-inorganic base material. An example of a raw material of an inorganic base material includes glass, silica gel and metal. An example of a raw material of an organic base material includes a synthetic polymer such as crosslinked polyvinyl alcohol, crosslinked polyacrylate, crosslinked polyacrylamide and crosslinked polystyrene; and a polysaccharide such as crystalline cellulose, crosslinked cellulose, crosslinked agarose and crosslinked dextran. An example of the commercially available insoluble base material includes a porous cellulose gel "GCL2000", "Sephacryl S-1000" prepared by crosslinking allyl dextran and methylene bisacrylamide through a covalent bond, an acrylate base material "Toyopearl", an agarose crosslinked base material "Sepharose CL4B" and a cellulose crosslinked base material "Cellufine". The insoluble base material usable in the present invention is not restricted to the above exemplified base materials.

A surface area of the insoluble base material usable in the present invention is preferably large and the insoluble base material preferably has many fine pores having an appropriate size and is porous, since the thiol group-including compound is supported on the insoluble base material. A form of the insoluble base material may be any one of beads, monolith, fiber and membrane such as hollow fiber, and may be optionally selected.

The insoluble base material can be reacted with the thiol group of the thiol group-including compound to form a covalent bond, since the insoluble base material has a functional group to be reacted with a thiol group on the surface. An example of such a functional group to be reacted with the thiol group includes epoxy group, carbonyl group, cyano group, toluenesulfonyl group, methanesulfonyl group, 2,2,2-trifluoroethanesulfonyl group and hydrazino group. The insoluble base material may be reacted with epichlorohydrin, diglycidyl ether, cyanogen bromide, tosyl chloride, mesyl chloride, tresyl chloride, hydrazine, a periodate salt or the like in order to introduce a functional group to be reacted with the thiol group on the surface of the insoluble base material.

A condition of Step B is not particularly restricted as long as the reaction liquid of Step A containing the thiol group-including compound is contacted with the insoluble base material. The reaction may be conducted in a neutral condition, or the reaction may be conducted in a basic condition. Specifically, pH of the reaction liquid of Step B, i.e. a mixture of the reaction liquid of Step A and the insoluble base material, is preferably adjusted to 6 or more and 11 or less. When the pH is 6 or more, the thiol group of the thiol group-including compound may be efficiently reacted with the reactive functional group of the insoluble base material more surely. On the one hand, when the pH is 11 or less, a denaturation of the thiol group-including compound may be suppressed more surely. The pH is more preferably 7 or more and 10 or less.

A base to adjust the reaction liquid of Step B to be basic is not particularly restricted as long as the base does not inhibit the reaction, and is exemplified by a hydrogencarbonate salt of an alkali metal, such as sodium hydrogencarbonate and potassium hydrogencarbonate; a carbonate salt of an alkali metal, such as sodium carbonate and potassium carbonate; a carbonate salt of an alkaline earth metal, such as calcium carbonate; a hydroxide of an alkali metal, such as sodium hydroxide and potassium hydroxide; and a hydroxide of an alkaline earth metal, such as calcium hydroxide.

A base to adjust the reaction liquid of Step B to be basic may be appropriately added. For example, a base may be added to the reaction liquid of Step A and then the insoluble base material or a dispersion liquid thereof may be mixed; a base may be added to a dispersion liquid of the insoluble base material and then the reaction liquid of Step A may be mixed; or the reaction liquid of Step A and the insoluble base material or a dispersion liquid thereof may be mixed and then a base may be added thereto. Alternatively, for example, a buffer solution of an appropriate pH range may be used as a solvent of a dispersion liquid of the insoluble base material.

A reaction condition of Step B may be appropriately adjusted. For example, a reaction temperature may be adjusted to 1° C. or higher and 50° C. or lower. A reaction time may be adjusted to 30 minutes or more and 24 hours or less. When the thiol group-including compound is supported on the insoluble base material, the reaction may be conducted under a reductive atmosphere in order to suppress a dimerization of the thiol group-including compound. On the one hand, Step B of the present invention may be implemented under an oxidative atmosphere such as an air atmosphere, since the thiol group-including organic reducing agent and/or the inorganic reducing agent used in Step A remains.

A general posttreatment may be executed after the reaction. For example, the carrier on which the thiol group-including compound is supported may be separated from the reaction liquid by filtration, centrifugation or the like after the reaction, and the carrier may be washed with water or the like. An amount of the thiol group-including compound supported on the carrier can be indirectly calculated from the amount of the used thiol group-including compound and the amount of the thiol group-including compound remaining in the reaction liquid.

The carrier on which the thiol group-including compound is supported by the present invention method can be used for purifying a compound having an affinity for the thiol group-including compound. Such a purification method can be performed in accordance with an affinity column chromatography purification method for an immunoglobulin. Specifically, a liquid sample containing a target compound having an affinity for the thiol group-including compound is prepared. An example of the sample includes blood, plasma, serum, culture fluid and homogenate of cultured cell. The sample is generally adjusted to be neutral or nearly neutral. Separately, an affinity column is prepared by filling a column with the carrier of the present invention. A compound having an affinity for the thiol group-including compound is selectively adsorbed on the carrier by flowing the sample through the column. Then, an appropriate amount of a neutral or nearly neutral buffer solution is flowed through the affinity column to wash an inside of the column. The target compound is adsorbed on the carrier at this point of time. Next, the target compound can be purified with high purity by flowing an acidic buffer solution having an appropriate pH through the column to elute the target compound. A substance to accelerate a dissociation of the target compound from the matrix may be added to an acidic buffer solution for the elution.

The carrier on which the thiol group-including compound is supported by the present invention method can be also used for detecting a compound having an affinity for the thiol group-including compound. For example, many of the thiol group-including compounds are supported on a substrate composed of glass and resin usable for protein microarray by the present invention method to detect and identify a compound having an affinity for the thiol group-including compound. In addition, the thiol group-including compound is supported on a sensor chip for an analytical instrument utilizing surface plasmon resonance or biolayer interferometry by the present invention method to detect and identify a compound having an affinity for the thiol group-including compound.

The present application claims the benefit of the priority date of Japanese patent application No. 2019-57650 filed on Mar. 26, 2019. All of the contents of the Japanese patent application No. 2019-57650 filed on Mar. 26, 2019, are incorporated by reference herein.

EXAMPLES

The present invention is hereinafter described in more detail with Examples. The present invention is, however, not restricted to the following Examples in any way, and it is possible to work the present invention according to the Examples with an additional appropriate change within the range of the above descriptions and the following descriptions. Such a changed embodiment is also included in the technical scope of the present invention.

Example 1

(1) Production and Treatment of Protein G

Protein G that had one cysteine residue per one molecule was produced in accordance with the method of Example 1 described in WO 2016/031902. In addition, 1.0 mol/L dithiothreitol aqueous solution was prepared by dissolving dithiothreitol manufactured by FUJIFILM Wako Pure Chemical (1.54 g) in water and further adding water thereto to adjust a whole amount to 10 mL. Furthermore, 1.0 mol/L sodium sulfite aqueous solution was prepared by dissolving sodium sulfite manufactured by KISHIDA CHEMICAL (6.3 g) in water and further adding water thereto to adjust a whole amount to 50 mL.

To 37 mg/mL solution of the produced Protein G (1.9 kg, 4.6 mmol), the 1.0 mol/L dithiothreitol aqueous solution (4.5 mL, 4.5 mmol) was added and further the 1.0 mol/L sodium sulfite aqueous solution (19 mL, 19 mmol) was added to be reacted at 4° C. for 11 hours.

(2) Measurement of Monomer Content Amount

A phosphate buffer solution was prepared by dissolving Dulbecco's PBS (−) manufactured by FUJIFILM Wako Pure Chemical in water in a concentration of 9.6 g/L. The reaction solution obtained by the above-described (1) (50 μL) was diluted by adding the phosphate buffer solution (1.7 mL). Then, the diluted reaction solution was analyzed by high performance liquid chromatography in the following condition, and a ratio of Protein G monomer to a total of Protein G oligomer such as dimer and Protein G monomer was calculated on the basis of peak areas.

Chromatography system: "alliace" manufactured by Nihon Waters

Detection: UV (280 nm)

Moving phase: phosphate buffer solution (pH 7.4) prepared by dissolving Dulbecco's PBS (−) manufactured by FUJIFILM Wako Pure Chemical in water in a concentration of 9.6 g/L Column: "Superdex 75 10/300" manufactured by GE Healthcare Column temperature: 25° C.

Flow speed: 0.5 mL/min

Sample injection volume: 50 μL

Monomer content amount (%)=[peak area of Protein G monomer/(peak area of Protein G monomer+ peak area of Protein G oligomer)]×100

As a result, a content amount of Protein G monomer was 86%.

(3) Support on Insoluble Base Material

A gel of a crosslinked cellulose particle was prepared as an insoluble base material by the method described in JP 2009-242770 A. The crosslinked cellulose particle gel (3.3 L) was dispersed in water so that a total liquid amount was adjusted to 4.0 L. To the dispersion liquid, 2.0 mol/L sodium hydroxide aqueous solution (0.5 kg) was added. The mixture was stirred at 33° C. for 30 minutes. Then, 1,4-butanediol diglycidyl ether (3.45 kg) was added thereto, and the mixture was stirred for 7 hours to introduce an epoxy group on the surface of the insoluble base material. Next, an epoxy group-containing insoluble base material was obtained by washing with a sufficient amount of water.

The epoxy group-containing insoluble base material (3.3 L) was dispersed in 150 mM sodium phosphate-1 mM EDTA buffer solution (pH 8.5), and a total liquid amount was adjusted to 4.2 L. Then, the Protein G-containing mixture solution obtained in the above (1) (1.87 kg) and 150 mM sodium phosphate-1 mM EDTA buffer solution (pH 8.5, 0.49 kg) were added thereto, and the mixture was stirred at 30° C. for 35 minutes. Separately, sodium sulfate was dissolved in 150 mM sodium phosphate-1 mM EDTA buffer solution (pH 8.5) to prepare 2.5 mol/L sodium sulfate solution. The thus obtained 2.5 mol/L sodium sulfate solution (3.3 kg) was added to the above mixed liquid, and the mixture was stirred for 3 hours to support Protein G on the insoluble base material. Subsequently, the insoluble base material was washed with 150 mM sodium phosphate-1 mM EDTA buffer solution (10 L). The washing liquid was obtained at the washing, and a content amount of Protein G in the washing liquid was measured using an ultra violet-visible spectrophotometer manufactured by Shimadzu Corporation. The rate of the Protein G supported on the insoluble base material was calculated from the amount of the used Protein G and the amount of the Protein G contained in the washing liquid; as a result, the rate was 84%.

Example 2

Protein G that had one cysteine residue per one molecule was prepared similarly to the above-described Example 1(1). A 1.0 mol/L dithiothreitol aqueous solution (1.0 µL, 1.0 µmol) and a 1.0 mol/L sodium sulfite aqueous solution (1.0 µL, 1.0 µmol) were added to a 37 mg/mL solution of the prepared Protein G (0.41 mL, 1.0 µmol) for the reaction at 4° C. for 20 hours. The mixture solution after the reaction (50 µL) was diluted by adding a phosphate buffer solution (1.7 mL), and a monomer content amount was measured in accordance with the method of the above-described Example 1(2); as a result, the monomer content amount was 80%.

Example 3

Protein G that had one cysteine residue per one molecule was prepared similarly to the above-described Example 1(1). In addition, a 0.5 mol/L dithioerythritol aqueous solution was prepared by dissolving dithioerythritol manufactured by FUJIFILM Wako Pure Chemical (0.1546 g) in water and further adding water to adjust the total amount to 2 mL. Furthermore, a 0.5 mol/L sodium sulfite aqueous solution was prepared by dissolving sodium sulfite manufactured by KISHIDA CHEMICAL (0.126 g) in water and further adding water to adjust the total amount to 2 mL. In addition, a phosphate buffer solution (pH 7.4) was prepared by dissolving Dulbecco's PBS (-) manufactured by FUJIFILM Wako Pure Chemical in water in a concentration of 9.6 g/L.

The 0.5 mol/L dithioerythritol aqueous solution (1 µL, 0.5 µmol) and further the 0.5 mol/L sodium sulfite aqueous solution (1 µL, 0.5 µmol) were added to a 37 mg/mL solution of the prepared Protein G (0.205 mL, 0.5 µmol) for the reaction at 4° C. for 20 hours. The mixture solution after the reaction (50 µL) was diluted by adding the phosphate buffer solution (1.7 mL), and a monomer content amount in the diluted solution was measured in accordance with the method of the above-described Example 1(2); as a result, the monomer content amount was 82%.

Example 4

Protein G that had one cysteine residue per one molecule was prepared similarly to the above-described Example 1(1). In addition, a 0.5 mol/L 1-thioglycerol aqueous solution was prepared by dissolving 1-thioglycerol manufactured by Tokyo Chemical Industry (0.1083 g) in water and further adding water to adjust the total amount to 2 mL. Furthermore, a 0.5 mol/L sodium sulfite aqueous solution was prepared by dissolving sodium sulfite manufactured by KISHIDA CHEMICAL (0.126 g) in water and further adding water to adjust the total amount to 2 mL. In addition, a phosphate buffer solution (pH 7.4) was prepared by dissolving Dulbecco's PBS (-) manufactured by FUJIFILM Wako Pure Chemical in water in a concentration of 9.6 g/L.

The 0.5 mol/L 1-thioglycerol aqueous solution (1 µL, 0.5 µmol) and further the 0.5 mol/L sodium sulfite aqueous solution (1 µL, 0.5 µmol) were added to a 37 mg/mL solution of the prepared Protein G (0.205 mL, 0.5 µmol) for the reaction at 4° C. for 20 hours. The mixture solution after the reaction (50 µL) was diluted by adding the phosphate buffer solution (1.7 mL), and a monomer content amount in the diluted solution was measured in accordance with the method of the above-described Example 1(2); as a result, the monomer content amount was 75%.

Example 5

Protein G that had one cysteine residue per one molecule was prepared similarly to the above-described Example 1(1). In addition, a 0.5 mol/L dithiothreitol aqueous solution was prepared by dissolving dithiothreitol manufactured by FUJIFILM Wako Pure Chemical (0.1546 g) in water and further adding water to adjust the total amount to 2 mL. Furthermore, a 0.5 mol/L sodium thiosulfate aqueous solution was prepared by dissolving sodium thiosulfate pentahydrate manufactured by FUJIFILM Wako Pure Chemical (0.2483 g) in water and further adding water to adjust the total amount to 2 mL. In addition, a phosphate buffer solution (pH 7.4) was prepared by dissolving Dulbecco's PBS (-) manufactured by FUJIFILM Wako Pure Chemical in water in a concentration of 9.6 g/L.

The 0.5 mol/L dithiothreitol aqueous solution (1 µL, 0.5 µmol) and further the 0.5 mol/L sodium thiosulfate aqueous solution (1 µL, 0.5 µmol) were added to a 37 mg/mL solution of the prepared Protein G (0.205 mL, 0.5 µmol) for the reaction at 4° C. for 20 hours. The mixture solution after the reaction (50 µL) was diluted by adding the phosphate buffer solution (1.7 mL), and a monomer content amount in the diluted solution was measured in accordance with the method of the above-described Example 1(2); as a result, the monomer content amount was 78%.

Example 6

Protein G that had one cysteine residue per one molecule was prepared similarly to the above-described Example 1(1). In addition, a 0.5 mol/L dithioerythritol aqueous solution was prepared by dissolving dithioerythritol manufactured by FUJIFILM Wako Pure Chemical (0.1546 g) in water and further adding water to adjust the total amount to 2 mL. Furthermore, a 0.5 mol/L sodium thiosulfate aqueous solution was prepared by dissolving sodium thiosulfate pentahydrate manufactured by FUJIFILM Wako Pure Chemical (0.2483 g) in water and further adding water to adjust the total amount to 2 mL. In addition, a phosphate buffer solution (pH 7.4) was prepared by dissolving Dulbecco's PBS (−) manufactured by FUJIFILM Wako Pure Chemical in water in a concentration of 9.6 g/L.

The 0.5 mol/L dithioerythritol aqueous solution (1 μL, 0.5 μmol) and further the 0.5 mol/L sodium thiosulfate aqueous solution (1 μL, 0.5 μmol) were added to a 37 mg/mL solution of the prepared Protein G (0.205 mL, 0.5 μmol) for the reaction at 4° C. for 20 hours. The mixture solution after the reaction (50 μL) was diluted by adding the phosphate buffer solution (1.7 mL), and a monomer content amount in the diluted solution was measured in accordance with the method of the above-described Example 1(2); as a result, the monomer content amount was 77%.

Comparative Example 1

(1) Preparation and Treatment of Protein G

Protein G that had one cysteine residue per one molecule was prepared similarly to the above-described Example 1(1). Separately, a phosphate buffer solution (pH 7.4) was prepared by dissolving Dulbecco's PBS (−) manufactured by FUJIFILM Wako Pure Chemical in water in a concentration of 9.6 g/L. A 37 mg/mL solution of the prepared Protein G (50 μL, 0.12 μmol) was diluted by adding the phosphate buffer solution (1.7 mL), and a monomer content amount was measured in accordance with the method of the above-described Example 1(2); as a result, the monomer content amount was 20%.

(2) Supporting on Insoluble Base Material

The epoxy group-containing insoluble base material prepared similarly to the above-described Example 1(3) (3.0 mL) was dispersed in 150 mM sodium phosphate-1 mM EDTA buffer solution so that a total liquid amount was adjusted to 3.8 mL. Then, the untreated Protein G solution of Comparative example 1(1) (1.69 mL) and 150 mM sodium phosphate-1 mM EDTA buffer solution (0.55 mL) were added thereto, and the mixture was stirred at 30° C. for 30 minutes. Then, a 2.5 mol/L sodium sulfate solution (2.4 mL) was added, and the mixture was further stirred for 3 hours to support Protein G on the insoluble base material. Subsequently, the insoluble base material was washed with 10 mL of 150 mM sodium phosphate-1 mM EDTA buffer solution. The washing liquid was obtained at the washing, and a content amount of Protein G in the washing liquid was measured using an ultra violet-visible spectrophotometer manufactured by Shimadzu Corporation. The rate of the Protein G supported on the insoluble base material was calculated from the amount of the used Protein G and the amount of the Protein G contained in the washing liquid; as a result, the rate was 35%.

Comparative Example 2

(1) Preparation and Treatment of Protein G

Protein G that had one cysteine residue per one molecule was prepared similarly to the above-described Example 1(1). A 1.0 mol/L dithiothreitol aqueous solution (23 μL, 23 μmol) was added to a 37 mg/mL solution of the prepared Protein G (1.9 mL, 4.6 μmol) for the reaction at 4° C. for 20 hours. Separately, a phosphate buffer solution (pH 7.4) was prepared by dissolving Dulbecco's PBS (−) manufactured by FUJIFILM Wako Pure Chemical in water in a concentration of 9.6 g/L. The mixture solution after the reaction (50 μL) was diluted by adding the phosphate buffer solution (1.7 mL), and a monomer content amount was measured in accordance with the method of the above-described Example 1(2); as a result, the monomer content amount was 84%.

(2) Supporting on Insoluble Base Material

The epoxy group-containing insoluble base material prepared similarly to the above-described Example 1(3) (3.3 mL) was dispersed in 150 mM sodium phosphate-1 mM EDTA buffer solution so that a total liquid amount was adjusted to 4 mL. Then, the Protein G-containing mixture solution obtained in Comparative example 1(1) (1.89 mL) and 150 mM sodium phosphate-1 mM EDTA buffer solution (0.6 mL) were added thereto, and the mixture was stirred at 30° C. for 30 minutes. Then, a 2.5 mol/L sodium sulfate solution (2.6 mL) was added, and the mixture was further stirred for 3 hours to support Protein G on the insoluble base material. Subsequently, the insoluble base material was washed with 150 mM sodium phosphate-1 mM EDTA buffer solution (10 mL). The washing liquid was obtained at the washing, and a content amount of Protein G in the washing liquid was measured using an ultra violet-visible spectrophotometer manufactured by Shimadzu Corporation. The rate of the Protein G supported on the insoluble base material was calculated from the amount of the used Protein G and the amount of the Protein G contained in the washing liquid; as a result, the rate was 72%.

Comparative Example 3

Protein G that had one cysteine residue per one molecule was prepared similarly to the above-described Example 1(1). A 1.0 mol/L sodium sulfite aqueous solution (5.0 μL, 5.0 μmol) was added to a 37 mg/mL solution of the prepared Protein G (0.41 mL, 1.0 μmol) for the reaction at 4° C. for 20 hours. Separately, a phosphate buffer solution (pH 7.4) was prepared by dissolving Dulbecco's PBS (−) manufactured by FUJIFILM Wako Pure Chemical in water in a concentration of 9.6 g/L. The mixture solution after the reaction (50 μL) was diluted by adding the phosphate buffer solution (1.7 mL), and a monomer content amount was measured in accordance with the method of the above-described Example 1(2); as a result, the monomer content amount was 65%.

Consideration

TABLE 1

| | Thiol group-including organic reducing agent | Inorganic reducing agent | Content amount of monomer | Support yield |
|---|---|---|---|---|
| Example 1 | dithiothreitol | sodium sulfite | 86% | 84% |
| Example 2 | dithiothreitol | sodium sulfite | 80% | — |
| Example 3 | dithioerythritol | sodium sulfite | 82% | — |
| Example 4 | 1-thioglycerol | sodium sulfite | 75% | — |

TABLE 1-continued

| | Thiol group-including organic reducing agent | Inorganic reducing agent | Content amount of monomer | Support yield |
|---|---|---|---|---|
| Example 5 | dithiothreitol | sodium thiosulfate | 78% | — |
| Example 6 | dithioerythritol | sodium thiosulfate | 77% | — |
| Comparative example 1 | — | — | 20% | 35% |
| Comparative example 2 | dithiothreitol | — | 84% | 72% |
| Comparative example 3 | — | sodium sulfite | 65% | — |

When Protein G containing a cysteine residue was not treated with a reducing agent, Protein G might be dimerized due to a formation of a disulfide bond and thus a content amount of a Protein G monomer was small and a supported amount on the base material was small as Comparative example 1.

When Protein G containing a cysteine residue was treated with only dithiothreitol as a thiol group-including organic reducing agent, an amount of supported Protein G was relatively decreased as Comparative example 2. The reason is considered to be that dithiothreitol might be supported on the base material through a thiol group.

Furthermore, when Protein G containing a cysteine residue was treated with only an inorganic reducing agent, a content amount of a Protein G monomer was decreased as Comparative example 3. The reason is considered to be that a dimerization of Protein G due to a formation of a disulfide bond could not be sufficiently suppressed by an inorganic reducing agent only.

When Protein G was treated with both of a thiol group-including organic reducing agent and an inorganic reducing agent, a monomer content amount was maintained to be high as Examples 1 to 6 unlike in the case of the above-described Comparative examples 1 to 3. A reaction to immobilize Protein G was not tested in Examples 2 to 6, but a supporting yield may be similar to Example 1 or higher if an immobilization reaction is carried out in Examples 2 to 6, since the supporting yield was high in Example 1 and a total use amount of reducing agents in Examples 2 to 6 was smaller than that in Example 1 and thus an impact on an immobilization reaction by reducing agents may be small in Examples 2 to 6.

The invention claimed is:

1. A method for supporting a thiol group-including compound on an insoluble base material, the method comprising:
   Step A: treating a thiol group-including compound with a thiol group-including organic reducing agent and an inorganic reducing agent in a solvent, and
   Step B: contacting the insoluble base material with the solvent after the thiol group-including compound is treated with the thiol group-including organic reducing agent and the inorganic reducing agent in Step A.

2. The method according to claim 1, wherein the ratio of the number of thiol groups in 1 mole of the thiol group-including organic reducing agent to the number of thiol groups in 1 mole of the thiol group-including compound is ≥1:1.

3. The method according to claim 1, wherein 1 or more mole of the inorganic reducing agent is used per 1 mole of the thiol group in the thiol group-including compound.

4. The method according to claim 1, wherein the thiol group-including compound is a thiol group-including peptide.

5. The method according to claim 1, wherein the thiol group-including organic reducing agent is at least one of dithiothreitol, 1-thioglycerol or dithioerythitol.

6. The method according to claim 1, wherein the inorganic reducing agent is at least one member selected from the group consisting of a sulfite salt, a bisulfite salt, a pyrosulfite salt, a thiosulfate salt and a dithionite salt.

7. The method according to claim 1, wherein said Step A and said Step B are implemented under standard air atmosphere.

8. A method for supporting a thiol group-including compound on an insoluble base material, the method comprising:
   Step A: treating a thiol group-including compound with a thiol group-including organic reducing agent and an inorganic reducing agent in a solvent,
   Step B: contacting the insoluble base material with the solvent after the thiol group-including compound is treated with the thiol group-including organic reducing agent and the inorganic reducing agent in Step A,
   wherein the thiol group-including compound is one or more selected from the group consisting of a peptide comprising a thiol group, cysteine, ethanethiol, aminoethanethiol, benzylthiol, thiophenol, polyethylene glycol of which one or more hydroxy groups are transformed into thiol groups, and polyvinyl alcohol of which one or more hydroxy groups are transformed into thiol groups.

9. The method according to claim 8, wherein the thiol group-including organic reducing agent is at least one of dithiothreitol, 1-thioglycerol or dithioerythitol.

10. The method according to claim 8, wherein the inorganic reducing agent is at least one member selected from the group consisting of a sulfite salt, a bisulfite salt, a pyrosulfite salt, a thiosulfate salt and a dithionite salt.

11. The method according to claim 8, wherein the thiol group-including organic reducing agent is at least one of dithiothreitol, 1-thioglycerol or dithioerythitol, and the inorganic reducing agent is at least one member selected from the group consisting of a sulfite salt, a bisulfite salt, a pyrosulfite salt, a thiosulfate salt and a dithionite salt.

12. The method according to claim 8, wherein the thiol group-including organic reducing agent comprises at least one of dithiothreitol, 1-thioglycerol or dithioerythritol and the inorganic reducing agent comprises at least one member selected from the group consisting of a sulfite salt and a thiosulfate salt.

13. The method according to claim 8, wherein the thiol group-including organic reducing agent is present in an amount such that the number of the thiol groups in the thiol group-including organic reducing agent is 1 time or more by mole to 8 times or less by mole to one mole of the thiol group of the thiol-group including compound and the amount of the inorganic reducing agent to 1 mole of the thiol group in the thiol group-including compound is 1 time or more by mole to 50 times or less.

14. A method for supporting a thiol group-including compound on an insoluble base material, the method comprising:

Step A: treating a thiol group-including peptide with a thiol group-including organic reducing agent and an inorganic reducing agent in a solvent, Step B: contacting the insoluble base material with the solvent containing the thiol group-including organic reducing agent and an inorganic reducing agent after the thiol group-including compound is treated with the thiol group-including organic reducing agent and the inorganic reducing agent in Step A, wherein the thiol group-including compound is one or more selected from the group consisting of a peptide comprising a thiol group, cysteine, ethanethiol, aminoethanethiol, benzylthiol, thiophenol, polyethylene glycol of which one or more hydroxy groups are transformed into thiol groups, and polyvinyl alcohol of which one or more hydroxy groups are transformed into thiol groups.

15. The method according to claim 14, wherein said peptide comprises an oligo peptite, a protein, a protein fragment or two or more peptides linked with a peptide bond.

16. The method according to claim 14, wherein said peptide comprises Protein A, Protein G, Protein L and variants thereof.

17. The method according to claim 14, wherein said peptide comprises Protein G, or a variant thereof.

18. The method according to claim 1, wherein the thiol group-including organic reducing agent is present in an amount such that the number of the thiol groups in the thiol group-including organic reducing agent is 1 time or more by mole to 8 times or less by mole to one mole of the thiol group of the thiol-group including compound and the amount of the inorganic reducing agent to 1 mole of the thiol group in the thiol group-including compound is 1 time or more by mole to 50 times or less.

19. The method according to claim 14, wherein the thiol group-including organic reducing agent is present in an amount such that the number of the thiol groups in the thiol group-including organic reducing agent is 1 time or more by mole to 8 times or less by mole to one mole of the thiol group of the thiol-group including compound and the amount of the inorganic reducing agent to 1 mole of the thiol group in the thiol group-including compound is 1 time or more by mole to 50 times or less.

* * * * *